United States Patent [19]

Houghten et al.

[11] Patent Number: 5,441,936

[45] Date of Patent: Aug. 15, 1995

[54] ANTIVIRAL PEPTIDES

[75] Inventors: Richard A. Houghten, Solana Beach; Patricia A. Weber, San Diego, both of Calif.

[73] Assignee: Houghten Pharmaceuticals, Inc., San Diego, Calif.

[21] Appl. No.: 163,370

[22] Filed: Dec. 7, 1993

[51] Int. Cl.$^6$ .................. A61K 38/08; C07K 7/06
[52] U.S. Cl. ........................ 514/16; 530/329
[58] Field of Search ................ 514/16; 530/329

[56] References Cited

FOREIGN PATENT DOCUMENTS

WO9010646A 9/1990 WIPO .

OTHER PUBLICATIONS

Houghten, Richard A. et al. "Generation and Use of Synthetic Peptide Combinatorial Libraries for Basic Research and Drug Discovery." Nature 354:84–86 (1991).

*Primary Examiner*—Howard E. Schain
*Assistant Examiner*—Benet Prickril
*Attorney, Agent, or Firm*—Campbell and Flores

[57] ABSTRACT

The present invention provides antiviral peptides having the general structure, Arg-Arg-Trp-Trp-Cys-Arg-X, where X is an amino acid or an amino acid analog, the stereochemistry of the amino acids or amino acid analogs can be (D)- or (L)-amino acids and the amino and carboxy termini of the peptide can be modified. The invention also provides a pharmaceutical composition comprising an antiviral peptide and methods of using an antiviral peptide in vitro or in vivo to reduce or inhibit a herpes simplex virus infection.

18 Claims, No Drawings

ANTIVIRAL PEPTIDES

BACKGROUND OF THE INVENTION

1 Field of the Invention

This invention relates generally to the fields of virology and molecular medicine and more specifically to antiviral peptides.

2. Background Information

Viral infections including those of herpes simplex virus (HSV) are common in the United States and around the world. Depending on socioeconomic class, anti-HSV antibodies can be identified in about 60% to 80% of the population of industrialized countries. New methods for detecting antibodies to HSV type 2 (HSV-2), which is a sexually transmitted disease, suggest that about 40 to 60 million individuals in the United States are infected with HSV-2. Based on figures for the spread of easily identified sexually transmitted diseases such as gonorrhea, it is estimated that 500,000 new cases of HSV-2 infection will occur annually.

The primary sites of HSV infection are the oral and genital mucosa. Viral replication at these sites can result in lesions such as skin vesicles or mucosal ulcers. HSV infection also can result in ocular keratitis, encephalitis and disseminated neonatal or adult infection. Recurrent outbreaks of HSV infection in a subject are common and can be induced, for example, by exposure to ultraviolet light, trauma to nerve ganglia, which harbor the latent virus, and treatment with immunosuppressive agents.

Currently, nucleoside analogs are used to treat viral infections, with acyclovir being the drug of choice for treating systemic herpes virus infection. Acyclovir can decrease the rate of recurrence in individuals plagued with frequent bouts of recurrent genital herpes. However, patients must be maintained on daily acyclovir therapy to prevent recurrence. As a result, acyclovir therapy for genital herpes is one of the more expensive treatments for a sexually transmitted disease. Nucleoside analogs also can be toxic to healthy cells and can induce resistant strains of herpes viruses, particularly in immunocompromised patients such as individuals suffering from AIDS.

HSV also causes about 500,000 cases of recurrent ocular keratitis per year and is second only to trauma as the leading cause of corneal blindness in the United States. As for other HSV infections, recurrent ocular HSV infection is treated using nucleoside analogs, with the dose and schedule of administration varying depending on the clinical classification of the disease. In general, however, treatment lasts for a minimum of 21 days and the antiviral agent is applied five times a day or every two hours, depending on the drug.

Despite treatment, healing of the cornea can take several weeks. In addition, the emergence of drug resistant virus strains during treatment can cause persistence or progression of clinical symptoms. Thus, the choice of effective antiviral agents is further limited in that these agents can induce drug resistant vital strains and cause toxicity to uninfected cells. A need exists, therefore, to identify a class of antiviral agents that are inexpensive to make and are useful for treating viral infections. The present invention satisfies this need and provides related advantages as well.

SUMMARY OF THE INVENTION

The present invention relates to antiviral peptides having the general structure, Arg-Arg-Trp-Trp-Cys-Arg-X, where X is an amino acid or an amino acid analog having a chiral center. Each amino acid or amino acid analog in a peptide as claimed herein can be a (D)- or an (L)-amino acid. In addition, the amino and carboxy termini of a peptide can be chemically modified. The invention also relates to pharmaceutical compositions comprising an antiviral peptide and to methods of using a claimed antiviral peptide in vitro or in vivo to reduce or inhibit a viral infection.

DETAILED DESCRIPTION OF THE INVENTION

The present invention relates to antiviral peptides, comprising:

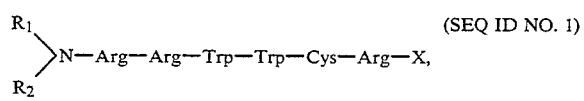 (SEQ ID NO. 1)

wherein X is

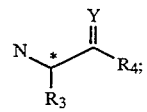

wherein
- $R_1$ is H, $COCH_3$, $CH_2Ph$, $CH_2CH_2Ph$, $COPh$, $COO$-t-butyl, $COOCH_2Ph$ or a linear or branched alkyl having 2 to 6 carbons;
- $R_2$ is H, $C_2H_5$ or $CH_2Ph$;
- $R_3$ is H, $CH_3$, $CH_2$—Ph, $CH_2$-pyridyl, $CH_2$-imidazole, $CH_2$-indole, $CH_a$—$(CH_2)_nCOOH$, $CH_2$—$(CH_2)_nCONHR_5$, $CH_2$—$(CH_2)_nNHR_5$, $CH_2$—$(CH_2)_nOH$, $CH_2$—$(CH_2)_nSR_5$, or $CH_2$—$(CH_2)_nNC(NH)NH_2$;
- $R_4$ is OH, $NH_2$, SH, $NHCH_3$, $N(CH_3)_2$, $NHCH_2Ph$, or $OR_5$; and
- $R_5$ is H, $CH_3$, or a linear or branched alkyl having 2 to 6 carbons; and wherein Ph is $C_6H_5$, Y is O or $H_2$, n is 0, 1, 2 or 3 and "*" denotes a chiral center, which can be either R or S. The peptides can be further modified, for example, by acetylation of the carboxy terminus, by amidation of the amino terminus or by chemical modification of a reactive amino acid side group.

The antiviral peptides described herein provide a significant advantage over currently used antiviral drugs such as nucleoside analogs. For example, antiviral therapy for recurrent ocular HSV infection varies depending on whether the disease is classified as epithelial (dendritic), disciform, infiltrative stromal disease or iritis. Epithelial disease commonly is treated topically using a nucleoside analog, such as trifluorothymidine, adenine arabinoside or idoxuridine. Treatment typically lasts for a minimum of 21 days and the antiviral agent is applied five times a day or every two hours, depending on the drug. Disciform disease, infiltrative stromal disease and iritis are treated with topical antiviral agents plus Varying doses of topical corticosteroids, depending on the extent of the disease.

Due to the prolonged treatment period required when nucleoside analogs are used to treat a viral infection, drug resistant virus strains can emerge. For example, an acyclovir resistant HSV type 1 strain was isolated from patients treated for keratitis. Evaluation of these patients revealed that the presence of the resistant virus was associated with persistence or progression of clinical symptoms during acyclovir therapy. Thus, the use of nucleoside analogs such as acyclovir is limited in that these agents can induce drug resistant viral strains. In addition, nucleoside analogs can cause toxicity to uninfected cells.

The present invention provides effective antiviral peptides, which, in general, are heptapeptides comprising the L- or D-amino acids or amino acid analogs described herein. Examples of such antiviral peptides include:

1) Ac-Arg-Arg-Trp-Trp-Cys-Arg-Ala-NH$_2$;
2) Ac-Arg-Arg-Trp-Trp-Cys-Arg-Arg-NH$_2$;
3) Ac-Arg-Arg-Trp-Trp-Cys-Arg-Asn-NH$_2$;
4) Ac-Arg-Arg-Trp-Trp-Cys-Arg-Asp-NH$_2$;
5) Ac-Arg-Arg-Trp-Trp-Cys-Arg-Cys-NH$_2$;
6) Ac-Arg-Arg-Trp-Trp-Cys-Arg-Glu-NH$_2$;
7) Ac-Arg-Arg-Trp-Trp-Cys-Arg-Gln-NH$_2$;
8) Ac-Arg-Arg-Trp-Trp-Cys-Arg-Gly-NH$_2$;
9) Ac-Arg-Arg-Trp-Trp-Cys-Arg-His-NH$_2$;
10) Ac-Arg-Arg-Trp-Trp-Cys-Arg-Ile-NH$_2$;
11) Ac-Arg-Arg-Trp-Trp-Cys-Arg-Leu-NH$_2$;
12) Ac-Arg-Arg-Trp-Trp-Cys-Arg-Lys-NH$_2$;
13) Ac-Arg-Arg-Trp-Trp-Cys-Arg-Met-NH$_2$;
14) Ac-Arg-Arg-Trp-Trp-Cys-Arg-Phe-NH$_2$;
15) Ac-Arg-Arg-Trp-Trp-Cys-Arg-Pro-NH$_2$;
16) Ac-Arg-Arg-Trp-Trp-Cys-Arg-Ser-NH$_2$;
17) Ac-Arg-Arg-Trp-Trp-Cys-Arg-Thr-NH$_2$;
18) Ac-Arg-Arg-Trp-Trp-Cys-Arg-Trp-NH$_2$;
19) Ac-Arg-Arg-Trp-Trp-Cys-Arg-Tyr-NH$_2$; and
20) Ac-Arg-Arg-Trp-Trp-Cys-Arg-Val-NH$_2$, where each amino acid is indicated by its three letter code and the stereochemistry is all D-amino acids, where "Ac" indicates the amino terminus of the peptide has been modified by acetylation and where "NH$_2$" indicates the carboxy terminus of the peptide has been modified by amidation. All peptide sequences shown herein are written in the conventional format, with the amino terminus at the left end of the sequence and the carboxy terminus at the right end of the sequence.

The use of peptide antiviral agents provides a preferred alternative to the current methods for treating viral infection. Peptides are versatile in that they can be designed, for example, to interrupt the viral life cycle by mechanisms that are different from those of nucleoside analogs or to act at a metabolic step where resistance is less likely to develop. Multiple targets exist where a peptide can interrupt a viral life cycle. For example, peptides can be designed to block a cellular receptor that a virus uses to enter the cell. Peptides also can be designed to block essential enzymes encoded by the virus. A particular nonapeptide has been reported to inhibit HSV-1 ribonucleotide reductase by binding to the large subunit of the enzyme, thereby preventing binding of the enzyme subunits. In addition, a series of tetrapeptides have been shown to inhibit ribonucleotide reductase. Other peptides can be designed to bind, for example, the viral proteinase, which is required for processing viral precursor proteins, thus rendering the virus unable to complete the packaging of an infectious virion. In addition, a specific 17-mer cationic peptide has been shown to directly inactivate herpes virus by a mechanism that may be similar to that exhibited by the defensin class of peptides isolated from mammalian neutrophils.

Peptides have the added advantage that they can be synthesized in large numbers at relatively low cost and they can be readily modified to exhibit diverse properties (see, for example, Rees et al., *Protein Engineering: A Practical Approach* (IRL Press 1992), which is incorporated herein by reference). Antiviral peptides such as those exemplified above were synthesized using a modification of the solid phase peptide synthesis method of Merrifield (*J. Am. Chem. Soc.*, 85:2149 (1964), which is incorporated herein by reference) or can be synthesized using standard solution methods well known in the art (see, for example, Bodanszky, M., *Principles of Peptide Synthesis* (Springer-Verlag, 1984), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

The claimed antiviral peptides were synthesized using amino acids or amino acid analogs, the active groups of which were protected as required using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

One skilled in the art would know that the choice of amino acids or amino acid analogs incorporated into a peptide will depend, in part, on the specific physical, chemical or biological characteristics required of the antiviral peptide. Such characteristics are determined, in part, by the route by which the antiviral peptide will be administered or the location in a subject to which the antiviral peptide will be directed. For example, the antiviral peptides exemplified above were synthesized using only (D)-amino acids. However, the skilled artisan would know that any or all of the amino acids in a peptide can be a naturally occurring (L)-amino acid or a non-naturally occurring (D)-amino acid.

As used herein, the term "amino acid" is generally meant to include naturally occurring proteogenic amino acids as well as non-naturally occurring amino acids such as amino acid analogs. In view of this broad definition, one skilled in the art would know that reference herein to an amino acid, unless specifically indicated otherwise, includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through well known metabolic pathways.

The choice of including an (L)- or a (D)-amino acid in an antiviral peptide of the present invention depends, in part, on the desired characteristics of the antiviral peptide. For example, the incorporation of one or more (D)-amino acids can confer increased stability on the peptide in vitro or in vivo. The incorporation of one or more (D)-amino acids also can increase or decrease the antiviral activity of the peptide as determined, for example, using the plaque forming assay described in Example II, below, or other well known methods for determining viral infectivity in vitro or in vivo. Thus, the construction of peptides comprising D-amino acids provides particularly useful antiviral peptides. However, in some cases it may be desirable to allow the peptide to remain active for only a short period of time. In those cases, the incorporation of one or more (L)-amino acids in the peptide can allow endogenous peptidases in a subject to digest the peptide in vivo, thereby limiting the subject's exposure to an active antiviral peptide. The skilled artisan can determine the desirable characteristics required Of an antiviral peptide by taking into consideration, for example, the age and general health of a subject and the extent of viral infection in the subject.

Selective modification of the reactive groups in a peptide also can impart desirable characteristics to an antiviral peptide. A peptide can be manipulated while still attached to the resin to obtain, for example, an N-terminal modified peptide such as the acetylated peptides exemplified above. Alternatively, the peptide can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus and methods for amidation of the C-terminus, as described in Example I. Similarly, methods for modifying the reactive side chain of an amino acids are well known to those skilled in the art of peptide synthesis. The choice of modifications made to the reactive groups present on the peptide will be determined by the characteristics that the skilled artisan requires in the peptide. A newly synthesized peptide can be purified using a method such as reverse phase high performance liquid chromatography (RP-HPLC), which is described in detail below (see Example I), or other methods of separation based on the size or charge of the peptide. Similarly, well known methods such as amino acid sequence analysis or mass spectrometry, which is described in Example I, are available for characterizing the structure of the antiviral peptide.

The invention also relates to pharmaceutical compositions comprising an antiviral peptide of the present invention and a pharmaceutically acceptable carrier. Pharmaceutically acceptable carriers are well known in the art and include aqueous solutions such as physiologically buffered saline or other solvents or vehicles such as glycols, glycerol, vegetables oils (eg., olive oil) or injectable organic esters. A pharmaceutically acceptable carrier can be used to administer an antiviral peptide to a cell in vitro or to a subject in vivo.

A pharmaceutically acceptable carrier can contain physiologically acceptable compounds that act, for example, to stabilize the antiviral peptide or increase or decrease the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and sorbic acid. One-skilled in the art would know that the choice of a pharmaceutically acceptable carrier, including a physiologically acceptable compound, depends, for example, on the route of administration of the antiviral peptide and on the particular physico-chemical characteristics of the specific antiviral peptide. For example, a physiologically acceptable compound such as aluminum monosterate or gelatin is particularly useful as a delaying agent, which prolongs the rate of absorption of a pharmaceutical composition administered to a subject by injection.

The invention further relates to methods of administering a pharmaceutical composition comprising an antiviral peptide as claimed herein to a subject in order to reduce or inhibit a viral infection that produces, for example, ocular keratitis, encephalitis or oral or genital lesions. As used herein, the phrase "reduce or inhibit" means that the severity of a viral infection is decreased as a result of the administration of an antiviral peptide. The determination that a viral infection is reduced or inhibited can be made, for example, using an in vitro plaque forming assay as described in Example II, below. Using such an assay, a reduced or inhibited viral infection can be identified by determining that the number of plaque forming units of virus in a sample is decreased following antiviral treatment as compared to the number of plaque forming units determined prior to treatment. In addition, the de! termination that a viral infection is reduced or inhibited in vivo can be made using, for example, a standard clinical determination such as observing the disappearance or decrease in the number or recurrence of virally-induced skin lesions. The skilled artisan would know various other routine methods for determining whether a viral infection has been reduced or inhibited in vitro or in vivo due to administration of an antiviral agent.

A pharmaceutical composition comprising an antiviral peptide of the present invention can be administered by various methods including orally, intravaginally, rectally, parenterally, intravenously, intramuscularly, subcutaneously, intraorbitally, intracapsularly, intraperitoneally, intracisternally or by passive or facilitated absorption through the skin using, for example, a skin patch or transdermal iontophoresis, respectively. The composition can be administered by bolus injection in a single dose, by multiple fractionated doses over a period of days or weeks or by continuous infusion. In addition, the composition can be administered over a sustained period of time, for example, using a dermal patch or an implant device such as a subdermal pump.

A pharmaceutical composition comprising an antiviral peptide of the present invention can be administered by injection, intubation or topically. Various methods of topical administration are useful and include, for example, passive topical administration such as by direct application of eye drops, an ointment or a powder or active topical administration such as by using a nasal spray or an inhalant. A pharmaceutical composition comprising an antiviral peptide also can be administered as a topical spray, in which case one component of the composition can be an appropriate propellant.

The pharmaceutical composition also can be incorporated, if desired, into liposomes, microspheres or other polymer matrices (see, for example, Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer. Liposomes, for example, are particularly useful for administering a pharmaceutical composition comprising an antiviral peptide to cell in tissue culture in order to reduce or inhibit viral infection of the cells. Such a method can be useful, for example, where the cells are to be used for an autologous transplant.

An effective amount of an antiviral peptide of the present invention can be used to reduce or inhibit a viral infection of cells in culture. As used herein, an "effective amount" is a concentration of an antiviral peptide required to reduce or inhibit a viral infection in vitro. An effective amount of an antiviral peptide, which can be about 1 to about 100 µg/ml of medium, can be readily determined using methods well known in the art, including the plaque forming assay described in Example II. As shown in Table 1, an effective amount of various antiviral peptides comprising D-amino acids inhibited HSV-1 infection in cells in culture (see, also, Example II). One skilled in the art would recognize that an effective amount of an antiviral peptide depends on several factors, including the activity of the antiviral peptide and the other components of the pharmacologically acceptable composition comprising the peptide. However, the skilled artisan can readily determine a concentration of an antiviral peptide that is useful as an effective amount based on the methods described herein (see Example II) or otherwise well known in the art. Thus, the compounds described herein can be used as medicaments for the treatment of viral pathologies.

TABLE I

Herpes Simplex Virus Type-1 Plaque Inhibition

| Peptide | IC$_{50}$ (µg/ml) |
|---|---|
| Ac—Arg—Arg—Trp—Trp—Cys—Arg—Ala—NH$_2$ | 35 |
| Ac—Arg—Arg—Trp—Trp—Cys—Arg—Arg—NH$_2$ | 62 |
| Ac—Arg—Arg—Trp—Trp—Cys—Arg—Asn—NH$_2$ | 85 |
| Ac—Arg—Arg—Trp—Trp—Cys—Arg—Asp—NH$_2$ | >100 |
| Ac—Arg—Arg—Trp—Trp—Cys—Arg—Cys—NH$_2$ | 50 |
| Ac—Arg—Arg—Trp—Trp—Cys—Arg—Glu—NH$_2$ | >100 |
| Ac—Arg—Arg—Trp—Trp—Cys—Arg—Gln—NH$_2$ | 37 |
| Ac—Arg—Arg—Trp—Trp—Cys—Arg—Gly—NH$_2$ | >100 |
| Ac—Arg—Arg—Trp—Trp—Cys—Arg—His—NH$_2$ | >100 |
| Ac—Arg—Arg—Trp—Trp—Cys—Arg—Ile—NH$_2$ | >100 |
| Ac—Arg—Arg—Trp—Trp—Cys—Arg—Leu—NH$_2$ | 61 |
| Ac—Axg—Arg—Trp—Trp—Cys—Arg—Lys—NH$_2$ | 50 |
| Ac—Arg—Arg—Trp—Trp—Cys—Arg—Met—NH$_2$ | >50 |
| Ac—Arg—Arg—Trp—Trp—Cys—Arg—Phe—NH$_2$ | 59 |
| Ac—Arg—Arg—Trp—Trp—Cys—Arg—Pro—NH$_2$ | >100 |
| Ac—Arg—Arg—Trp—Trp—Cys—Arg—Ser—NH$_2$ | >100 |
| Ac—Arg—Arg—Trp—Trp—Cys—Arg—Thr—NH$_2$ | >100 |
| Ac—Arg—Arg—Trp—Trp—Cys—Arg—Trp—NH$_2$ | 37 |
| Ac—Arg—Arg—Trp—Trp—Cys—Arg—Tyr—NH$_2$ | >100 |
| Ac—Arg—Arg—Trp—Trp—Cys—Arg—Val—NH$_2$ | 58 |

An effective amount of an antiviral peptide as claimed herein also can be used to inhibit a viral infection in a subject. As used herein, a "subject" means a mammal including a human. An effective amount of an antiviral peptide, which can be about 0.01 to about 100 mg/kg body weight, can be readily determined by considering the activity of the particular antiviral peptide being administered, the route of administration, the period over which the antiviral peptide is to be administered, the extent of viral infection and other factors known to those skilled in treating viral infections.

The following examples are intended to illustrate but not limit the present invention.

EXAMPLE I

Synthesis of An Antiviral Peptide Having the Amino Acid Sequence
Ac-Arg-Arg-Trp-Trp-Cys-Arg-Cys-NH2

This example describes the method of solid phase peptide synthesis used to synthesize an antiviral peptide having the sequence shown above.

MBHA resin containing t-BOC-cysteine was added to a reaction vessel suitable for solid phase peptide synthesis using the "tea bag" method described by Houghten (1985). The resin was washed 3x with methylene chloride and the t-BOC protecting group was removed using trifluoroacetic acid (TFA) containing 1–2% anisole in methylene chloride.

Following removal of the protective group, the resin was washed with methylene chloride, then treated with diisopropylethylamine. The nascent peptide was extended by adding 3.2 equivalents of di-tolulyl-BOC-arginine in dimethylformamide (DMF) and 3.0 equivalents of dicyclohexylcarbodiimide in DMF to the reaction vessel. The reaction was allowed to proceed for 25 min and the extent of reaction was monitored using ninhydrin. Following the addition of each amino acid residue, the resin was washed with methylene chloride and the procedure was repeated using the appropriate protected amino acid derivatives (Advanced Chemtech; Louisville, Ky.). The N-formyl-BOC protecting group on the tryptophan residues was removed using 20% piperidine in DMF.

The heptapeptide was acetylated at the amino terminus by treatment with acetic anhydride, then washed with methylene chloride and cleaved from the resin using anhydrous hydrogen fluoride containing 10% anisole. The reaction mixture was concentrated by evaporation and the residue was digested with aqueous acetic acid. The acetic acid fraction, which contained the digested sample, was removed and the residue was washed with water. The wash was added to the acetic acid fraction and the combined sample was concentrated. The resulting crude peptide was purified by RP-HPLC (Vydac, C-18 column, using a gradient of 1 to 60% solution B over 30 min (solution A is 0.1% TFA/water and solution B is 0.1% TFA/acetonitrile).

The peptide was determined to be greater than 90% pure by RP-HPLC (Vydac C-18 column, using a gradient of 5% to 55% solution B over 30 min; absorption was determined at 215 nm). The mass of the purified peptide was determined by plasma absorption mass spectrometry using a BioIon 20 Mass Analyzer, time of flight detector. The mass of the peptide was measured to be 1108.3, which corresponded with the expected molecular mass of 1108.

EXAMPLE II

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Arg  Arg  Trp  Trp  Cys  Arg  Xaa
    1                         5

Antiviral Peptides Inhibit Plaque Formation in MSV-1-Infected Cells

This example demonstrates that the antiviral peptides described herein can effectively inhibit virus growth in cells in vitro.

Vero cells were seeded into 24-well tissue culture plates 24 to 48 hr prior to performing the plaque assay. Herpes simplex type 1 virus (HSV-1) was diluted to 50 to 60 plaque forming units (pfu)/0.1 ml Medium 199 and 0.1 ml was added to the cells. Control cultures received 0.1 ml Medium 199 without HSV-1. Plates were incubated for 2 hr at 37° C. in 5% carbon dioxide.

Following incubation of the cells with or without HSV-1, the medium was removed by aspiration. The peptides to be tested for antiviral activity were diluted in Dulbecco's modified Eagle's medium supplemented with 0.2% human gamma globulin, 5% fetal bovine serum, 10 units/ml penicillin and 5µg/ml streptomycin and 1 ml of the peptide solution was added to each of duplicate wells. Medium only was added to wells labelled for input virus or cell controls.

Cells were observed by microscopy at 24 and 48 hr to identify toxicity due to the peptides. Following the incubation period, medium was removed by aspiration and the cultures were fixed using methanol and stained with 0.037% Geimsa for 45 min. The stain was removed and the plates were rinsed and allowed to air dry. The concentration of peptide that inhibited growth of 50% of the input HSV-1 (IC50) was determined for each peptide by counting the number of viral plaques present in the peptide-treated wells as compared with the input virus control wells.

Using the plaque inhibition assay, a peptide was considered to have no antiviral effect in this assay if greater than 100 µg/ml of the peptide was required to inhibit growth of 50% of the input HSV-1. As shown in Table I, more than half of the peptides examined had antiviral activity. For example, 50 µg/ml of the peptide described in Example I had a significant antiviral effect (see Table I, line 12). These results demonstrate that the plaque inhibition assay can be used to readily determine an effective amount of an antiviral peptide in vitro.

Although the invention has been described with reference to the examples above, it should be understood that various modifications can be made without departing from the spirit of the invention. Accordingly, the invention is limited only by the following claims.

We claim:

1. An antiviral peptide, comprising:

$$\begin{matrix} R_1 \\ \phantom{R}\diagdown \\ \phantom{RRR}N-Arg-Arg-Trp-Trp-Cys-Arg-X, \\ \phantom{R}\diagup \\ R_2 \end{matrix}$$ (SEQ ID NO. 1)

wherein X is $$\begin{matrix} & Y \\ & \| \\ N\diagdown\overset{*}{\phantom{C}}\diagup R_4; \\ & | \\ & R_3 \end{matrix}$$

wherein $R_1$ is H, $COCH_2$, $CH_2Ph$, $CH_2CH_2Ph$, COPh, COO-t-butyl, $COOCH_2Ph$ or a linear or branched alkyl having 2 to 6 carbons;

$R_2$ is H, $C_2H_5$ or $CH_2Ph$;

$R_3$ is H, $CH_3$, $CH_2$-Ph, $CH_2$-pyridyl, $CH_2$-imidazole, $CH_2$-indole, $CH_2-(CH_2)_2COOH$, $CH_2-(CH_2)_2CONHR_5$, $CH_2-(CH_2)_nNHR_5$, $CH_2-(CH_2)_nSR_5$, $CH_2-(CH_2)_nNC(NH)NH_2$; or $CH_2-(CH_2)_nOH$;

$R_4$ is OH, $NH_2$, SH, $NHCH_3$, $N(CH_3)_2$, $NHCH_2Ph$, or $OR_5$; and $R_5$ is H, $CH_3$, or a linear or branched alkyl having 2 to 6 carbons; and wherein Ph is $C_6H_5$, Y is O or Ha, n is 0, 1, 2 or 3 and "*" denotes a chiral center, which can be R or S.

2. The antiviral peptide of claim 1, wherein the amino acids comprising said peptide are independently selected from the group consisting of (D)-amino acids and (L) -amino acids.

3. The antiviral peptide of claim 1, wherein the amino acids comprising said peptide are all D-amino acids.

4. The antiviral peptide of claim 1, wherein the amino terminus is modified.

5. The antiviral peptide of claim 1, wherein the carboxy terminus is amidated.

6. The antiviral peptide of claim 1, wherein the amino terminus is acetylated and the carboxy terminus is amidated.

7. The antiviral peptide of claim 1, wherein $R_1$ is selected from the group consisting of H, $C_2H_5$ and CH2Ph and wherein $R_2$ is selected from the group consisting of H and COCH3.

8. The antiviral peptide of claim 1, wherein $R_1$ is the same moiety as $R_2$ and wherein said same moiety is selected from the group consisting of H, a linear alkyl having 2 to 6 carbons and a branched alkyl having 2 to 6 carbons.

9. An antiviral peptide, comprising: Ac-Arg-Arg-Trp-Trp-Cys-Arg-Cys-NH2, wherein said amino acids are D-amino acids.

10. The antiviral peptide of claim 7, wherein the carboxy terminus of said peptide is amidated.

11. A composition of matter comprising a pharmaceutically acceptable carrier and an antiviral peptide, said peptide comprising:

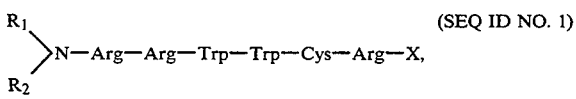

(SEQ ID NO. 1)

wherein X is

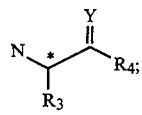

wherein
$R_1$ is H, COCH3, CH2Ph, CH2CH2Ph, COPh, COO-t-butyl, COOCH2Ph or a linear or branched alkyl having 2 to 6 carbons;
$R_2$ is H, C2H5 or CH2Ph;
$R_3$ is H, CH2, CH2—Ph, CH2-pyridyl, CH2-imidazole, CH2-indole, CH2-(CH2)$_n$COOH, CH2—(CH2)$_n$CONHR5, CH2—(CH2)$_n$NHR5, CH2—(CH2)$_n$SR5, CH2—(CH2)$_n$NC(NH)NH2 or CH2—(CH2)$_n$OH;
$R_4$ is OH, NH$_a$, SH, NHCH3, N(CH3)2, NHCH2Ph, or OR5; and $R_5$ is H, CH3, or a linear or branched alkyl having 2 to 6 carbons; and
wherein Ph is C6H5, Y is O or H$_s$, n is 0, 1, 2 or 3 and wherein "*" denotes a chiral center, which can be R or S.

12. A method of reducing or inhibiting a herpes simplex virus infection in a cell in vitro, comprising the steps of:
  a. adding an effective amount of the pharmaceutical composition of claim 11 to the cell; and
  b. contacting said cell with said pharmaceutical composition for a period of time sufficient to reduce or inhibit the herpes simplex virus infection in said cell.

13. A method of reducing or inhibiting a herpes simplex virus infection in a subject, comprising administering to the subject an effective amount of the pharmaceutical composition of claim 11.

14. The method of claim 13, wherein said administration is topical.

15. The method of claim 13, wherein said herpes simplex virus infection produces ocular keratitis.

16. The method of claim 13, wherein said herpes simplex virus infection produces encephalitis.

17. The method of claim 13, wherein said herpes simplex virus infection produces oral lesions.

18. The method of claim 13, wherein said herpes simplex virus infection produces genital lesions.

* * * * *

UNITED STATES PATENT AND TRADEMARK OFFICE
CERTIFICATE OF CORRECTION

PATENT NO. : 5,441,936

DATED : August 15, 1995

INVENTOR(S) : Houghten and Weber

It is certified that error appears in the above-identified patent and that said Letters Patent is hereby corrected as shown below:

Column 1, line 63, please delete "vital" and replace therefor with --viral--.

Column 2, line 39, please delete "$CH_\alpha(CH_2)_nCOOH,$" and replace therefor with --$CH_2-(CH_2)_nCOOH,$--

Column 2, line 51, please delete "acetylation" and replace therefore with --amidation--

Column 2, line 51, please delete "amidation" and replace therefor with --acetylation--

Column 5, line 23, please delete "Of" and replace therefor with --of--

Column 6, line 39, please delete "de! termination" and replace therefor with --determination--.

Column 8, line 15, please delete "NH2" and replace therefor with --$NH_2$--.

Column 9, line 25, please delete "MSV-1" and replace therefor with --HSV-1--

UNITED STATES PATENT AND TRADEMARK OFFICE
CERTIFICATE OF CORRECTION

PATENT NO. : 5,441,936
DATED : August 15, 1995
INVENTOR(S) : Houghten and Weber

It is certified that error appears in the above-indentified patent and that said Letters Patent is hereby corrected as shown below:

Column 9, line 29, please delete "we! 1" and replace therefor with --well--.

Column 9, line 52, please delete "(IC50)" and replace therefor with --($IC_{50}$)--.

Column 10, line 45, please delete $_2CONHR_5$," and replace therefor with --$_nCONHR_5$,--.

Column 10, line 52, please delete "Ha" and replace therefor with --$H_2$--.

Column 12, line 1, please delete "$CH_2$," and replace therefor with --$CH_3$,--.

Column 12, line 6, please delete "NH₀₄," and replace therefor with --$NH_2$,--.

Column 12, line 9, please delete "$H_s$," and replace therefor with --$H_2$,--.

Signed and Sealed this

Seventh Day of May, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,441,936
DATED        : Aug. 15, 1995
INVENTOR(S)  : Houghten et al.

It is certified that error appears in the above-identified patent and that said Letters Patent is hereby corrected as shown below:

In column 1, under the title "Antiviral Peptides" please insert the following

-- ACKNOWLEDGEMENT

This invention was made with government support under Grant No. 1R43-AI-36052-01 awarded by the National Institutes of Health. The government has certain rights in the invention.--

Signed and Sealed this

Twenty-sixth Day of May, 1998

*Attest:*

BRUCE LEHMAN

*Attesting Officer*         *Commissioner of Patents and Trademarks*